United States Patent [19]
Johnson et al.

[11] Patent Number: 5,813,280
[45] Date of Patent: Sep. 29, 1998

[54] ACOUSTIC RESONATOR FOR MEASURING FORCE

[75] Inventors: Ward L. Johnson, Louisville; George A. Alers, Boulder, both of Colo.; Bert A. Auld, Portola Valley, Calif.

[73] Assignee: The United States of America as represented by the Secretary of Commerce, Washington, D.C.

[21] Appl. No.: 708,393

[22] Filed: Sep. 4, 1996

Related U.S. Application Data

[60] Provisional application No. 60/021,051 Jul. 2, 1996.

[51] Int. Cl.$^6$ ........................................................ G01L 7/10
[52] U.S. Cl. ............................... 73/643; 73/763; 73/761
[58] Field of Search ................................ 73/862.59, 643, 73/580, 581, 760, 761, 862.21; 367/176, 82, 854.4

[56] References Cited

U.S. PATENT DOCUMENTS

| | | | |
|---|---|---|---|
| H1308 | 5/1994 | Winbow et al. | 367/176 |
| 852,647 | 5/1907 | Blake | 367/176 |
| 2,880,404 | 3/1959 | Harris | 367/176 |
| 3,186,222 | 6/1965 | Martin | 340/854.4 |
| 3,460,063 | 8/1969 | Houck et al. | 73/643 |
| 3,583,213 | 6/1971 | Houck et al. | 73/643 |
| 4,080,836 | 3/1978 | Thompson et al. | 73/597 |
| 4,522,071 | 6/1985 | Thompson | 73/597 |
| 4,777,824 | 10/1988 | Alers et al. | 73/643 |
| 5,205,176 | 4/1993 | Kibblewhite | 73/761 |

OTHER PUBLICATIONS

Alers, George A., Ward Johnson, E. Segal and B. A. Auld, Applications for measurement off shear–wave resonant modes in Cylinders, in Proceedings 1994 IEEE Ultrasonics Symposium, Nov. 1–4, 1994, Cannes, France.

Maxfield, B. W. and C. M. Fortunko, The design and use of electromagnetic acoustic wave transducers (EMATS), Materials Evaluation, 41, Nov. 1983.

Primary Examiner—Ronald L. Biegel
Attorney, Agent, or Firm—Holland & Hart LLP

[57] ABSTRACT

A force sensor including a cylindrical body having a central section and two distal sections wherein selected acoustic resonant modes are trapped in the central section and decays exponentially in the distal sections. An electromechanical acoustic transducer (EMAT) can be used to excite and detect the selected resonant modes in the central section. Force applied to the distal sections, including axial stress and torque, alter the resonant frequencies of the selected modes.

28 Claims, 10 Drawing Sheets

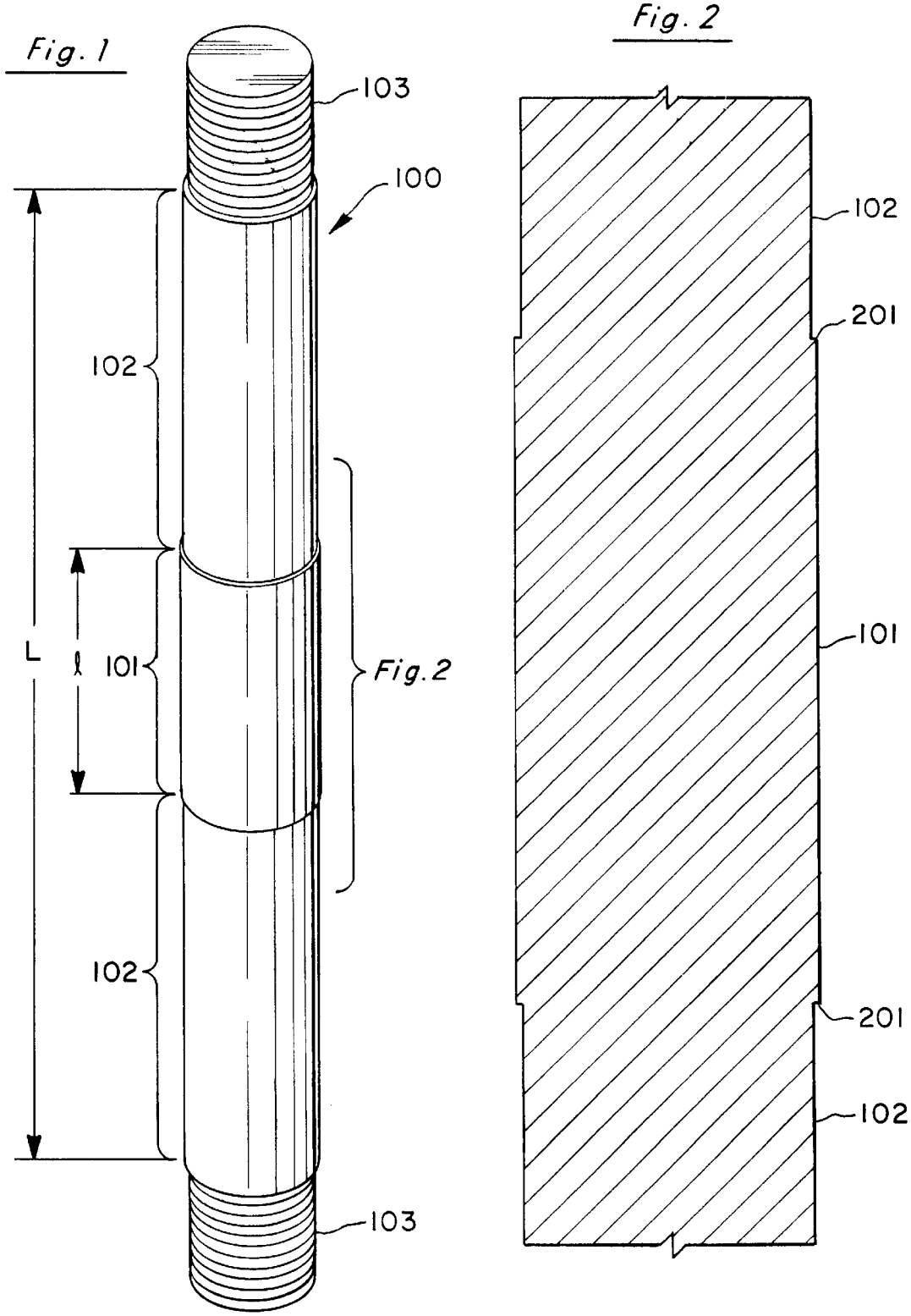

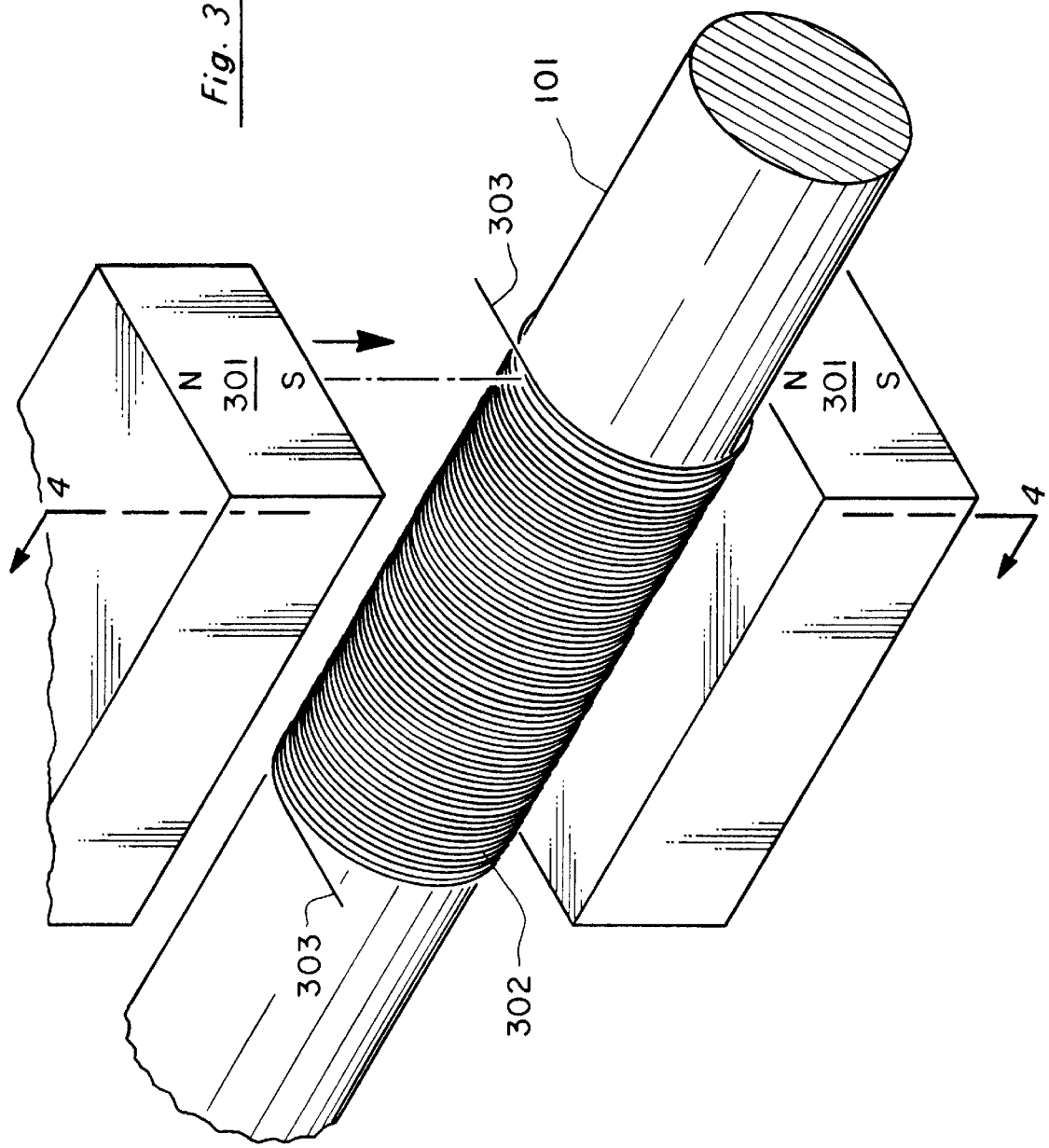

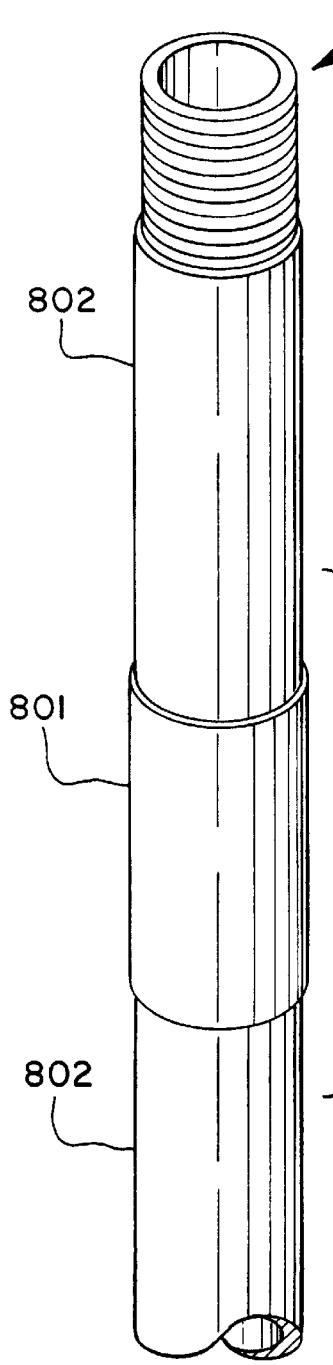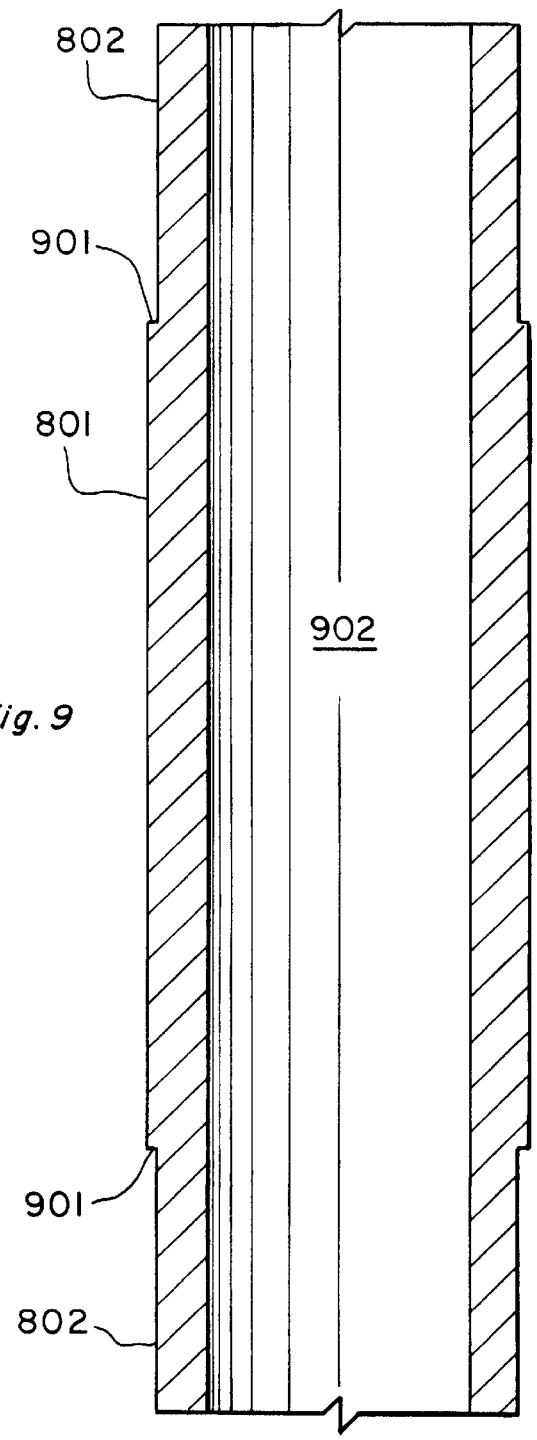

ACOUSTIC RESONATOR FOR MEASURING FORCE

This application is a continuation of provisional application Ser. No. 60/021,051 filed Jul. 2, 1996, now abandoned.

BACKGROUND OF THE INVENTION

1. Field of the Invention

The present invention relates, in general, to, an acoustic resonator and, more particularly, to an acoustic resonator that serves as a load-bearing element in devices for measuring force.

2. Statement of the Problem

It is often useful to be able to determine the amount of force applied to a load bearing element in a mechanical system. Force measurement is useful in, for example, weight measurement for heavy loads such as cargo, industrial materials, and trucks. Also, in bridges, buildings, and other man-made structures measurement of the static and dynamic forces acting on the structure is critical to both the construction and maintenance of a the structure. In vehicles and machinery, force measurement and monitoring is useful to study and predict component failure of the load bearing elements. Similarly, force measurement is useful to determine properties of materials and machine parts. In general, force measurements are useful in determining the structural integrity and safe service life of manufactured articles.

Force is commonly measured by strain gauges that are physically and mechanically coupled (e.g., by an adhesive) to a load-bearing member. The strain gauges generate an electrical signal in response to deformation of the load-bearing member. Although reliable and inexpensive, strain gauges suffer from error due to the physical coupling. Strain gauges are also temperature sensitive requiring additional circuitry to provide temperature compensation. Further, strain gauges are subject to wear and tear in harsh environments resulting in changing output characteristics over time.

Of greater interest are non-contact methods of force measurement. Non-contact measurements are typically preferred because they eliminate the errors associated with attachment of the sensor to the load bearing member and reduce the magnitude of error introduced by the measurement process. Several non-destructive and non-contact force evaluation methods are known. X-ray diffraction is used to measure the distance between planes of atoms in the load-bearing element. Displacement of the planes from their relaxed state indicates the presence of stress in the load-bearing element. X-ray diffraction is limited to surface layers, however, due to the penetration depth of X-rays, and can only be used on crystalline materials having orderly layers of atoms. Equipment cost, safety considerations, and bulk are drawbacks of this technology.

Ultrasonic techniques are also used to measure force. For example, U.S. Pat. No. 4,522,071 issued to Thompson entitled "Method and Apparatus for Measuring Stress" illustrates one ultrasonic technique. Also, U.S. Pat. No. 5,205, 176 issued to Kibblewhite entitled "Ultrasonic Load Cell with Transducer" shows another ultrasonic technique. Ultrasonic methods rely on the principle that the velocity of propagation of ultrasonic waves in a load-bearing element is influenced by stresses in the load-bearing element. Typically velocity of propagation is measured by acoustically coupling an ultrasonic transducer to the load-bearing element to be measured. An ultrasonic wave is propagated into the load bearing element. An ultrasonic detector is also coupled to the load bearing element to monitor changes in wave velocity. Wave velocity is determined by measuring time of flight between a wave transmitter and a wave detector.

Ultrasonic coupling is most often provided by physically contacting the load-bearing element as shown in U.S. Pat. No. 5,205,176. It is also possible to propagate and detect ultrasonic waves using electromagnetic acoustic transducers (EMATs) without physical contact as shown in U.S. Pat. No. 4,552,071, U.S. Pat. No. 3,460,063, and U.S. Pat. No. 3,583,213. One recognized difficulty in non-contact ultrasonic measurements is that it is difficult to generate a large amplitude ultrasonic wave without physically contacting the load-bearing element. EMATs have proven useful in generating ultrasonic waves, but require inconveniently large currents and magnetic fields to create large amplitude waves. The relatively poor coupling efficiency of an EMAT can be partially overcome by driving samples into resonance. In other words, instead of attempting to pass very high currents through the EMAT to generate short ultrasonic pulses, one can drive transducers with relatively modest and more practical currents over much longer periods of time, such that the mechanical oscillations approach their steady-state amplitude. Force measurements can then be correlated to changes in resonance characteristics rather than time-of-flight characteristics.

A resonance frequency measurement technique is suggested by George A. Alers et al. in "Applications for Measurements of Shear-Wave Resonant Modes in Cylinders" published in 1994 *IEEE Ultrasonics Symposium Proceedings* (November, 1994). Here it was recognized that EMATs could be used to create resonances in cylindrical bodies and that small changes in the resonant frequencies caused by a change in stress could be detected.

However, the accuracy of the technique suggested in the Alers et al. paper is limited by the dependence of the resonant modes on other variables. In particular, acoustic damping and temperature cause signal degradation. Alers et al. suggest that resonant frequencies of both torsional and flexural modes could be measured simultaneously and mathematically combined to provide temperature compensation. However, Alers et al. do not propose a solution to damping created by mechanical coupling between the load to be measured and the load cell.

Damping-related signal degradation results from a number of sources, one of which is that the ultrasonic waves are transmitted to the ends of the load-bearing member and energy escapes from the load cell through the mechanical coupling used to attach the load cell to the load to be measured. This results in signal loss and corresponding decrease in signal-to-noise ratio. Also, ultrasonic energy is reflected back to a location where the resonant frequency is being measured. These reflected waves interfere with the primary waves introduced by the transmitting EMAT, making measurement difficult or impossible. These factors are particularly troublesome in practical force measurement elements that must be mechanically attached at both ends to the load to be measured.

As a result of the above identified difficulties, the ultrasonic force measurement technique using EMATs to excite and detect an ultrasonic resonance in a cylindrical body proposed by Alers et al. has not been developed into a practical force measurement tool. A need remains for an inexpensive, reliable non-contact force measurement technique

3. Solution to the Problem

The above and other problems of prior art force measurement tools and techniques are solved by an EMAT resonance structure that substantially reduces or eliminates errors caused by reflections from portions of the load-bearing element that are distant from the resonance portion of the load-bearing element. By minimizing reflected energy, resonance conditions can be isolated from unknown and uncontrolled variables. Attention can be focused on resonant modes in a comparatively small portion of the load-bearing element for improved ease of measurement, reduced cost, and simple construction.

SUMMARY OF THE INVENTION

Briefly stated, the present invention involves a force sensor including a cylindrical body having a central section and two distal sections wherein selected acoustic resonant modes are trapped in the central section and have substantially smaller amplitude in the distal sections. The trapping is accomplished in a preferred example by making the diameter of the central section larger than the diameter of the distal sections. Force is applied to the cylindrical body via couplings at the distal ends. Because the resonant modes are trapped in the central section, they do not interact with the couplings at the distal ends. In this manner, acoustic energy loss to the load to be measured is reduced and signal quality improved. An electromagnetic acoustic transducer (EMAT) can be used to excite and detect the selected resonant modes in the central section. Force applied to the distal sections, including axial stress and torque, alter the resonant frequencies of the selected modes.

BRIEF DESCRIPTION OF THE DRAWING

FIG. 1 illustrates a perspective view of an acoustic resonator in accordance with a first embodiment of the present invention;

FIG. 2 shows an axial cross-section through a portion of the resonator of FIG. 1;

FIG. 3A is a perspective view of the acoustic resonator of FIG. 1 associated with non-contact sensor for exciting and detecting flexural modes;

FIG. 8 shows a third embodiment in accordance with the present invention;

FIG. 9 shows an axial cross section through a portion of the resonator of FIG. 8;

DETAILED DESCRIPTION OF THE DRAWING

1. Overview

The resonant vibrational frequencies of any object are a function of applied stress, since the third-order elastic constants introduce small stress-dependent terms in the stress-strain relation. This dependence can provide the basis for a device for measuring stress. However, the accuracy of such a device is limited by the dependence of the resonant modes on other environmental variables, in particular, external damping and temperature. Damping is increased when a load is applied to a resonator, since a path is provided for the escape of vibrational energy. This damping leads to a decrease in signal amplitude and changes in the resonant frequencies. The temperature dependence of elastic constants near room temperature is typically several hundredths of a percent per degree Celsius, and the corresponding changes in resonant frequencies can overshadow the effects of stress.

Figure 6:
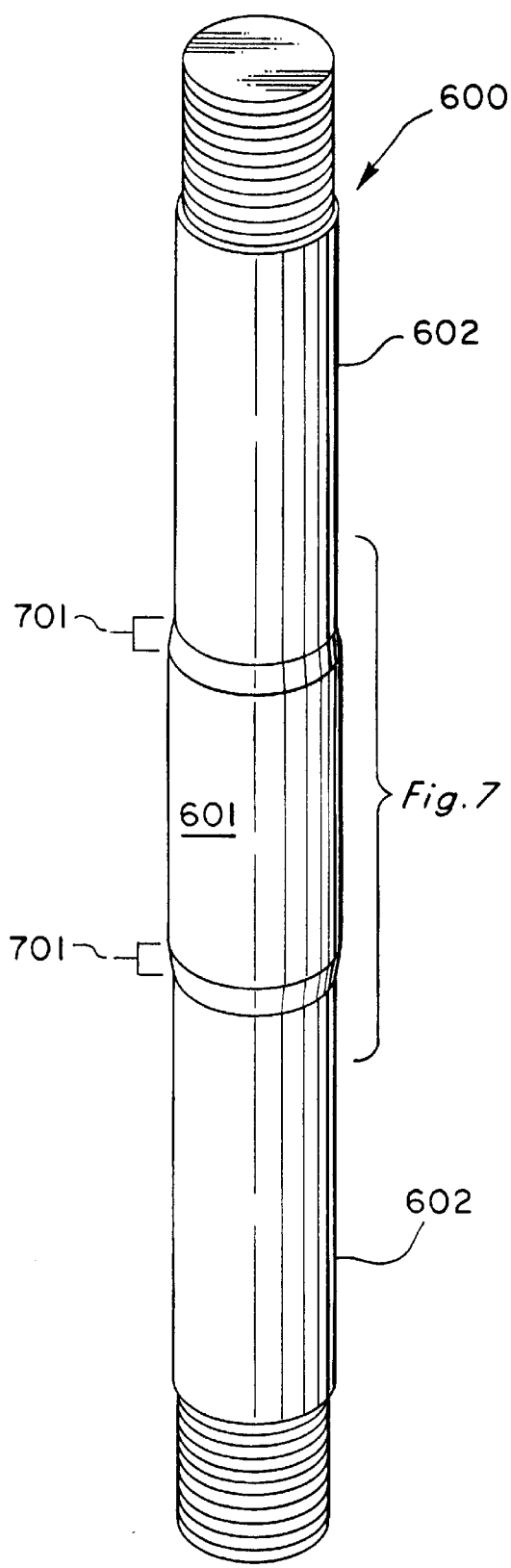
FIG. 6 illustrates a second embodiment acoustic resonator in accordance with the present invention.
Figure 7:
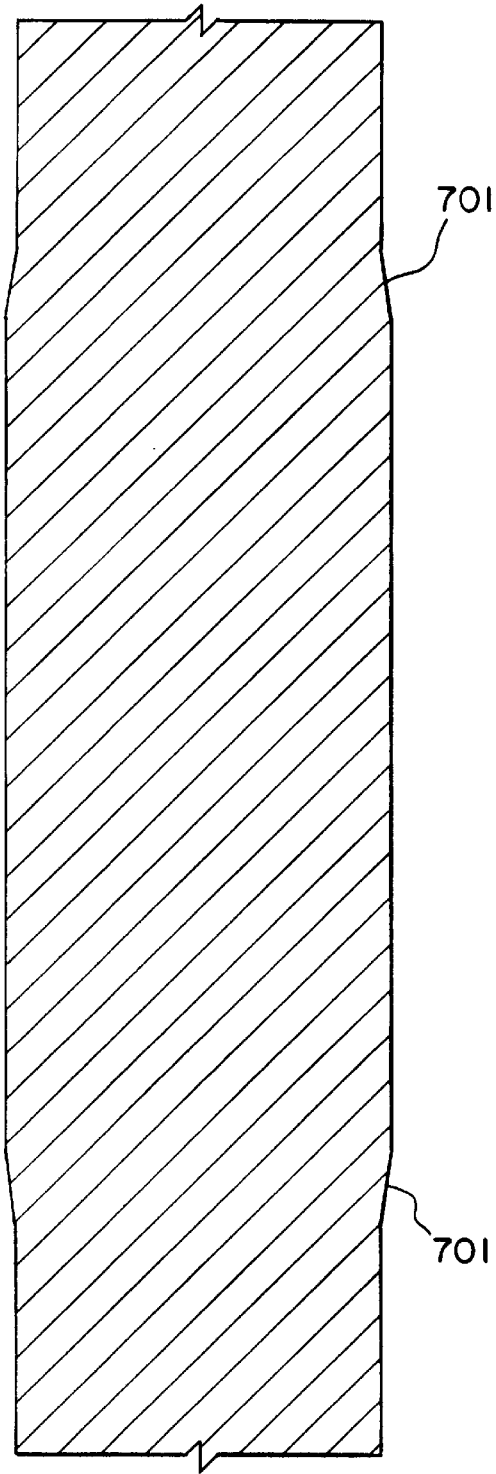
FIG. 7 shows an axial cross-section through a portion of the resonator of FIG. 6.
Figure 10:
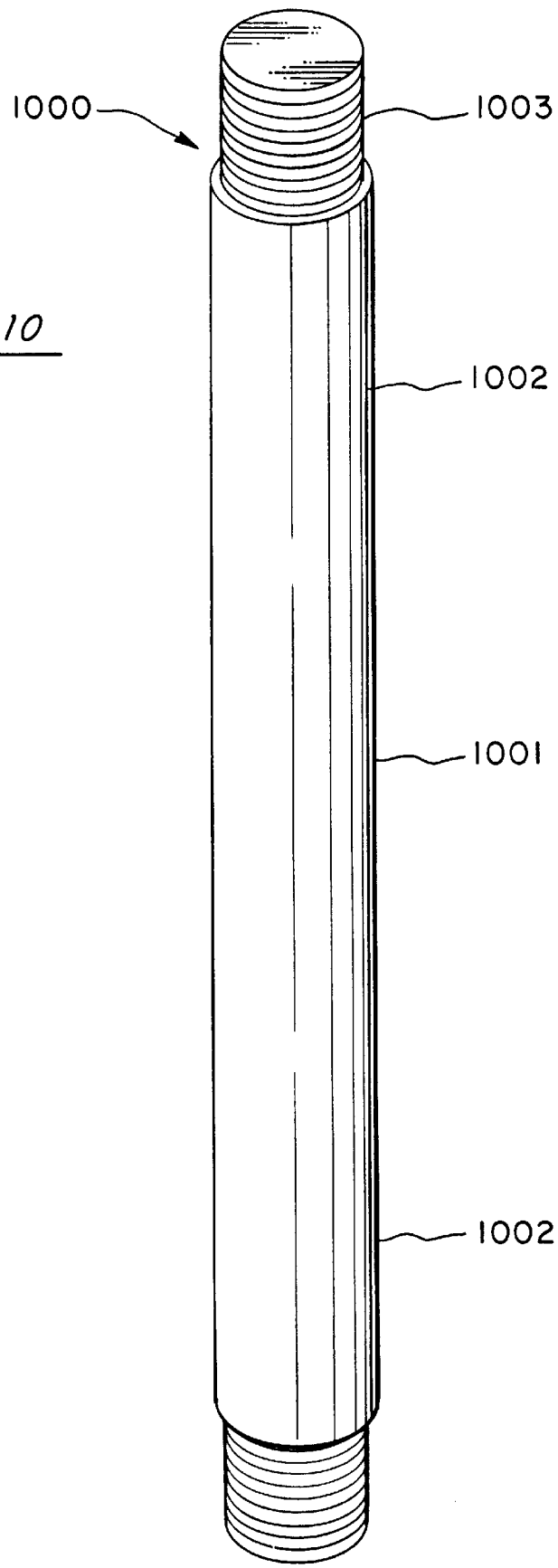
FIG. 10 illustrates another embodiment acoustic resonator in accordance with the present invention.

The present invention involves an acoustic resonator such as resonator 100 shown in FIGS. 1–4, resonator 600 shown in FIGS. 6–7, resonator 800 shown in FIGS. 8–9 and resonator 1000 shown in FIG. 10. The acoustic resonator in accordance with the present invention is particularly suitable for force measurement because it is largely immune from signal degradation caused by external damping because the vibrations are confined to the central region, away from the loading connections, and because the transducer uses non-contacting electromagnetic coupling mechanisms. Further, the resonator structures in accordance with the present invention are suitable for use with known temperature compensation techniques.

Essentially, the resonator in accordance with the present invention is used by exciting an acoustic vibration in the resonator and varying the frequency of the exciting energy until it resonates with a natural frequency of the resonator. The natural frequencies are determined by physical geometry, material choice, and environmental factors such as stress and temperature. Preferably, the resonant modes include "flexural" modes (excited and detected using an apparatus shown in FIG. 3A) as well as "torsional" modes (excited and detected using an apparatus shown in FIG. 3B).

Although other applications are contemplated, a significant use for the acoustic resonator in accordance with the present invention is as a load bearing element (i.e., a load cell) in a device for measuring force. Measurement of the force is accomplished by measuring the resonant frequencies of selected vibrational modes in a cylindrical body. The resonant frequencies vary with applied stress because the acoustic velocities of the material vary with the applied stress. The cylindrical body, which can be solid or hollow, preferably comprises a conductive material machined with variations in diameter that have the effect of localizing or trapping the selected vibrational modes in a central region of the cylindrical body.

An important practical advantage of vibrational trapping for force measurement is that it facilitates robust mechanical support at distal ends of the cylindrical body where only weak vibrations exist. The mechanical supports so located do not significantly affect the frequencies or damping of the resonant modes. The resonator in accordance with the present invention can be incorporated in devices for measuring a variety of stresses, including torque, uniaxial stress, and pressure of a gas or liquid inside a hollow cylinder (i.e., a tube).

Several applications are presently contemplated for the cylindrical trapped energy resonator in accordance with the present invention. One is a uniaxial stress measuring device (load cell). There is a wide range of potential applications for such a load cell because forces to be measured tend to be applied along axial directions of a solid or hollow metal cylinder. In these cases the acoustic velocities change as a result of these forces and the resonant frequencies change. The applied forces can be determined from measurements of the resonant frequencies.

Similar measurements can be performed with other types of forces on cylinders. For example, the pressure of a gas or liquid in a hollow cylinder can be measured. Experiments on measuring gas pressure in tubes without a trapped energy geometry have successfully demonstrated the principles of such a sensor. Also, torque on a trapped energy cylinder can be determined from resonant frequencies. This has significant application in machine and vehicle design where inexpensive torque sensors can provide a great deal of information about the operation and design of machinery.

The specific applications set out above are provided for example only and are not a limitation of the present invention. The present invention involves a fundamental method and apparatus for trapping acoustic waves in a cylindrical body. Other applications will be readily apparent to those skilled in the mechanical, measurement and instrumentation arts.

2. Theory

Vibrational energy trapping is important in the design of quartz crystal plate oscillators. The design of a cylindrical trapped-energy resonator in accordance with the present invention is similar to that used to design piezoelectric plate transducers, although the geometry is significantly different. The simplest geometry that results in trapping of modes in a solid cylinder is shown in FIG. 1. The diameter is larger over central portion 101, resulting in localization of vibrations in and near central portion 101. A similar effect is produced in a hollow tube by making the wall thicker over one region as shown in FIG. 8. Any geometry that traps vibrations must have a larger diameter (in the case of a solid cylinder) or a thicker wall (in the case of a hollow tube) over the regions where the vibrations are to be trapped, but the variations in diameter can be more complicated than that shown in FIG. 1. For example, the diameter could change gradually rather than being an abrupt step as illustrated in FIG. 6.

There are at least three general classes of modes that are relevant to the application of the present invention: torsional, radial, and flexural. The torsional modes consist of twisting motions around the axis of a cylinder with variations in magnitude and phase along both the axial and radial directions but not the azimuthal direction. These are described in detail in a publication by W. Johnson et al. in *the Journal of Acoustic Society of America*, Vol. 95, page 1413 (1994.) and need not be further described here for a complete understanding of the present invention. The radial modes consist of modes with displacements almost entirely in the radial direction with a magnitude and phase varying with position along the axial and radial directions. The flexural modes consist of displacement almost entirely in the axial direction with the magnitude and phase varying with axial position, radial position, and azimuthal position.

In a resonator in accordance with the present invention as shown in FIG. 1 a central portion of the cylindrical body has a larger diameter than the distal sections 102. The discontinuity at the interfaces between central section 101 and distal section 102 has the effect of preventing acoustic energy of certain modes from passing through distal sections 102 from central section 101. The acoustic energy of these certain modes is said to be "trapped". So long as one or more of the cylinder's natural resonant modes are trapped these can be excited and detected to monitor stress in the cylindrical body that will be largely independent of influences in the distal sections 102.

The choice of which resonant modes are to be excited and measured is made to maximize the trapping efficiency. In other words, the most efficiently trapped modes are those modes in which the least acoustic energy is coupled into distal sections 102 from central section 101. This occurs when the selected resonant modes are near "cutoff". Cutoff describes a condition when there is no variation of displacements along the axial direction. Flexural modes near cutoff are approximately "axial-shear", having displacements almost entirely in the axial direction.

The resonant frequencies ($\omega_t$) of trapped torsional modes that are symmetric about the center are approximately given by the equation:

$$\left[ \frac{\delta}{\Delta - \delta} \right]^{1/2} \tan \left[ \eta_t \left( \frac{\delta}{2} \right)^{1/2} \frac{l}{a} \right] \cong 1 \qquad \text{(Eq. 1)}$$

where:

$$\Delta \equiv 1 - \frac{b}{a} \frac{v_a}{v_b} \qquad \text{(Eq. 2)}$$

$$\delta \equiv (\omega_t - \omega_0)/\omega_0, \qquad \text{(Eq. 3)}$$

where $v_a$ is the velocity for shear plane-waves in central section 101, $v_b$ is the velocity for shear plane-waves in distal sections 102, $\omega_t$ is the angular frequency of the trapped torsional mode and $\eta_t$ is one of the infinite set of constants that satisfies the radial boundary condition of a uniform cylinder, $J_2(\eta_t)=0$, where $J_2$ is the Bessel function of the first kind of order 2. In Eq. 3 $\omega_0$ is the corresponding "cutoff" resonant frequency given by the equation:

$$\omega_0 = \eta_t v_a/a \qquad \text{(Eq. 4).}$$

Equations describing displacements of torsional modes in cylindrical bodies can be developed for each of central section 101 and both distal sections 103. By imposing the boundary conditions of continuity at the interface between central section 101 and distal sections 102 it can be shown that for resonant modes to be trapped in central sections 101, the relationship:

$$\eta_t v_a/a \leq \omega_t < \eta_t v_b/b \qquad \text{(Eq. 5)}$$

must be satisfied where $v_a$ is the velocity for shear plane-waves in central section 101, $v_b$ is the velocity for shear plane-waves in distal sections 102, and $\omega_t$ is the frequency of the trapped torsional mode.

The relationship set out in Eq. 5 makes evident that the range of trapped frequencies is determined not only by the radii of central section 101 and distal sections 102 (i.e., a and b in Eq. 5) but also by the velocity of shear plane-waves v in the various sections. Hence, trapping can be improved by varying the material composition of central section 101 from that of distal sections 102 so as to vary the ratio of v:radius from one section to the next. One embodiment described below in reference to FIG. 10 actually relies on this property to eliminate the step height (i.e., set a=b) and rely entirely on the change in velocity of shear plane-waves to establish trapping.

A theory for trapped flexural modes is not available, but experimental results show trapping performance similar to that of the torsional modes analyzed above. Flexural modes are established, for example, by a solenoid wound EMAT such as shown in FIG. 3A that excites and detects modes with a phase variation of $2\pi$ around the circumference of cylinder 100 and displacements primarily in the axial direction.

By solving the displacement equation for the boundary condition of zero stress on the outer cylindrical surface at resonance, the wave numbers ($\eta_f$) of resonant flexural modes can be determined. For the experimental structure described above, the first five values of $\eta_f$ were 1.84118, 5.33144, 8.53632, 11.70600 and 14.86359. These specific wave numbers are presented here only for purposes of completeness and are not a limitation of the function or structure of the present invention. Experimentally, the flexural mode with $\eta_f$=14.86359 was found to be affected only slightly by mechanical contact near mounting surfaces 103. This result indicates that the mode is highly localized in central section 101.

The theoretical and mathematical proof of the resonant trapping features in accordance with the present invention presented here is greatly simplified to ease understanding. A detailed mathematical derivation and supporting experimental measurements are presented in a paper entitled "Trapped Torsional Modes in Solid Cylinders" by the inventors of the present invention and to be published by the *Journal of the Acoustical Society of America* in July, 1996.

3. Resonator Design

Resonators 100, 600 and 800 and 1000 in accordance with various embodiments of the present invention are constructed as cylindrical bodies comprising conductive material. The choice of conductive material allows convenient non-contact excitation of ultrasonic waves in the cylindrical body and does not play a role in the trapping feature in accordance with the present invention. Acoustic waves are excited in a conductive material by application of an electromagnetic field that is converted to mechanical energy by the Lorenz effect. Optionally, magnetic material can be used in which case, acoustic waves are excited by magnetostriction in response to a magnetic field. Hence, the preferred choice of conductive (or magnetic) materials is a practical choice to enable non-contact excitation and detection of resonance in the cylindrical body, and may not be required in some applications.

Referring now to the embodiment shown in FIG. 1, the step height at the junction between regions 101 and 102 on the order of a hundred micrometers for an example structure having a diameter in the order of 2.5 centimeters. Although larger step heights do increase the exponential decay of trapped mode energy in distal sections 102 according to the equations presented above, these equations are approximations that become less accurate with increased step height. Actually, a larger step height results in increased mixing of the trapped modes with modes that are not trapped. This mode mixing makes the trapping less efficient. On the other hand, as the step height is made smaller, the rate of exponential decay in distal sections 102 decreases, which also affects trapping efficiency. A preferred range of about 0.5% to 2.0% of the radius of central section 101 is acceptable. An abrupt step can be formed by machining material away from the surface of distal sections 102 or by plating additional material onto central section 101. In either case, the end result is an abrupt step 201, best seen in FIG. 2.

In one experimental structure, resonator 100 was machined from a 2.54 cm diameter solid aluminum rod using a 2024-T351 alloy. The radius in central section 101 was approximately 11.9 mm and the radius in distal sections 102 was approximately 11.8 mm. The length of central section 101 was approximately 51.2 mm. Mounting surfaces 103 began at approximately 76 mm from the interface of central section 101 and distal sections 102 giving a total length of 203.2 mm. The specific parameters for the experimental structure are given only by way of example and the present invention is not limited to the specific dimensions given.

In the experimental structure, the trapped torsional mode was the lowest-frequency solution of Eq. 1 presented earlier with $\eta_t$=11.61984. The trapped mode is axially symmetric about the middle of central section 101 and has $\delta=1.21\times10^{-3}$. This particular mode was selected because the resonant peak was strong and well separated from other peaks, but any of several observed trapped torsional modes could have been used effectively.

One metric for describing the step height is calculated by normalizing the step height difference using the formula $$\Delta = \frac{a-b}{a}$$

where $\Delta$ is the normalized step height, a is the radius of central section 101, and b is the radius of distal sections 102. The step height $\Delta$ can be arbitrarily small if cylinder 100 is sufficiently long. Experiments with $\Delta$ in the range of 0.01 to 0.02 have demonstrated trapping, however, a wider range is believed to be acceptable.

Mounting surfaces such as threaded ends 103 are formed on distal sections 102. Mounting surface 103 can take any form or shape to meet the needs of a particular application. For example, pins, rivets, bolts, adhesives, and the like may be used. Mounting surfaces 103 can be adapted to any of these applications. A key advantage of the acoustic resonator in accordance with the present invention is that mounting surfaces 103 are located sufficiently far from central section 101 such that mechanical changes caused by coupling surfaces 103 to another object do not affect resonant frequencies in central section 101. This allows mounting surfaces 103 to be coupled to sources of stress, strain, and force of any variety without affecting the accuracy or resolution of force measurements.

The length of central section 101 is indicated by l in FIG. 1. In the preferred embodiments, distal sections 102 are symmetrical about central section 101. Asymmetrical cylinders may complicate analysis, but can still result in resonant mode trapping. The overall length of apparatus 100 excluding mounting surfaces 103 is indicated by L in FIG. 1. In practice, to have low vibrational amplitudes at the ends of distal sections 102 in a cylinder of uniform elastic constant (as compared to the embodiment described in reference to FIG. 10), a sufficiently large ratio of total length (L in FIG. 1) to central section radius (a in FIG. 1) is desirable.

Resonator 100 including mounting surfaces 103 is preferably formed from a single cylinder or tube of metal such as aluminum alloy. Aluminum is desirable because of its high conductivity and substantial strength per unit weight. High conductivity materials are desirable because they are able to interact with electromagnetic energy to create acoustic vibrations in resonator 100 using non-contacting transducers. Strength is an important asset in a load cell as the load cell can be placed as a load bearing member in a structure or machine thereby greatly reducing the impact on the machine's size, cost, and performance.

4. Electromechanical Acoustic Transducer Interface

Co-pending patent application Ser. No. 08/285,018 assigned to the assignee of the present invention and commonly invented by some of the inventors of the present application describes an electromagnetic acoustic transducer (EMAT) design that is useful for exciting and detecting the resonant modes in the acoustic resonator of the present invention. The preferred EMAT sensor is used to both excite and detect acoustic energy in the cylinder. The EMAT sensor is a preferred method to be used in accordance with the present invention but the invention does not include or is not limited by this preferred implementation.

Figure 3B:
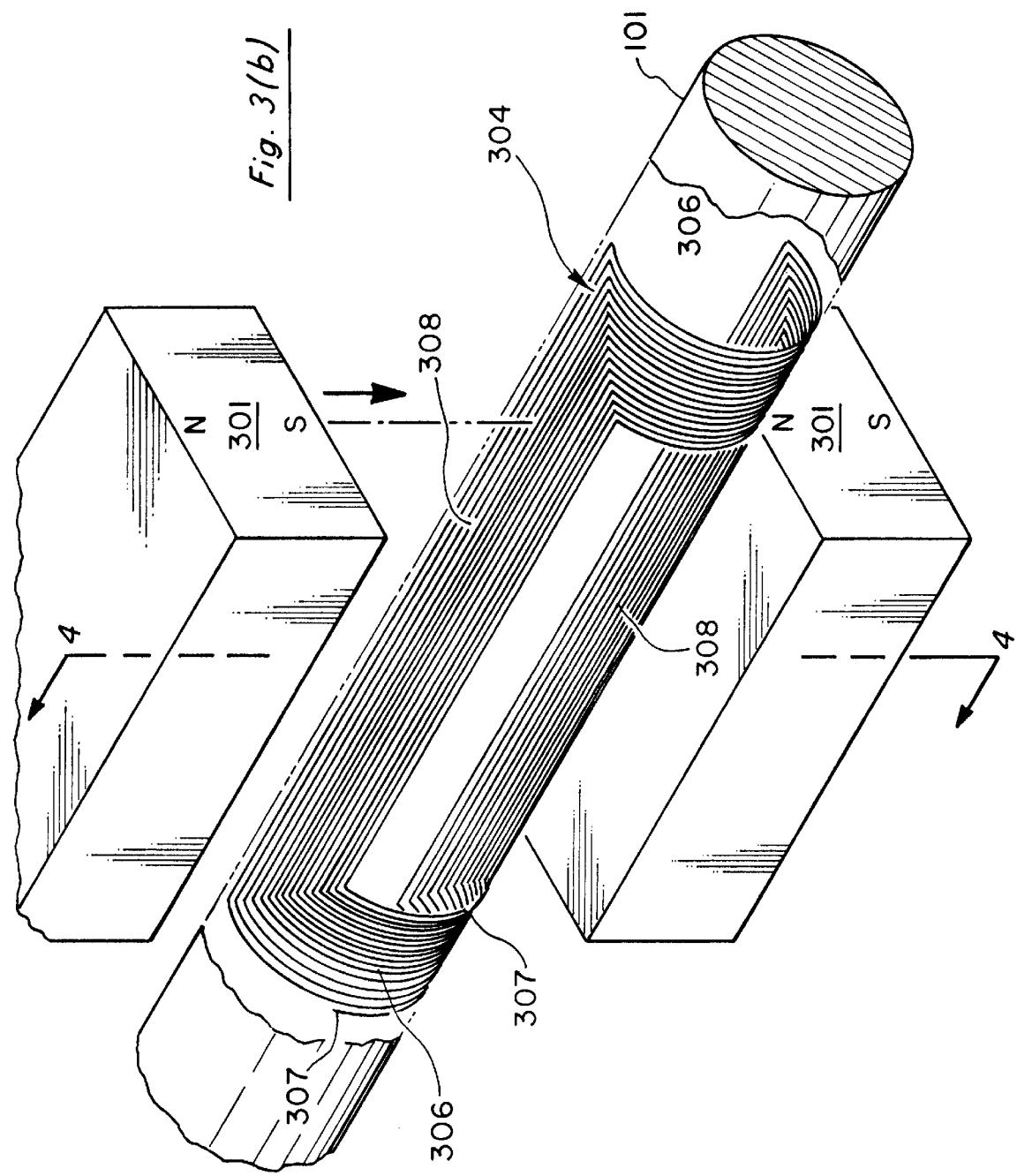
FIG. 3B is a perspective view of the acoustic resonator of FIG. 1 associated with a second type of non-contact sensor for exciting and detecting torsional modes.
Figure 4:
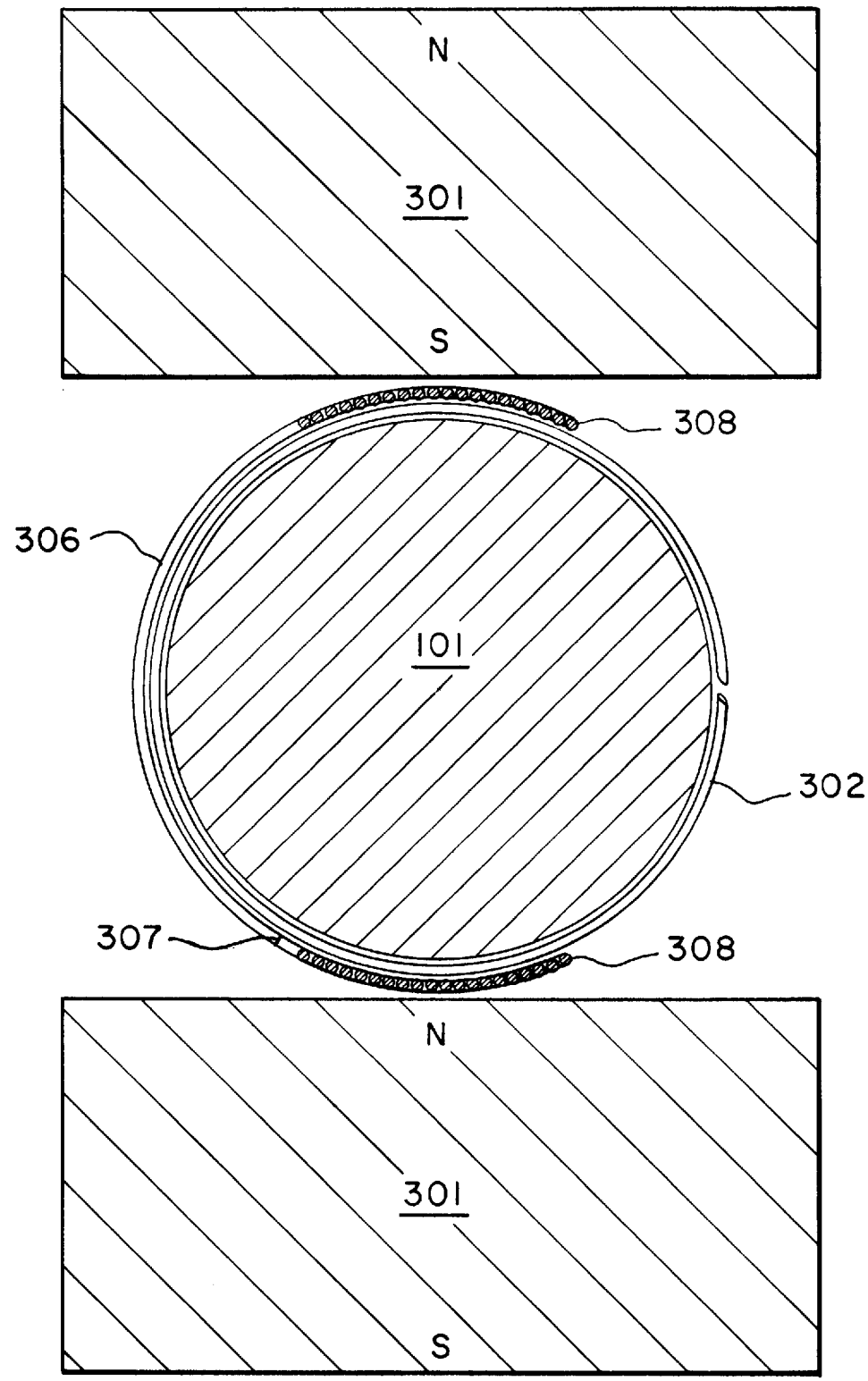
FIG. 4 shows a partial cross section through the resonator in accordance with the present invention with the first and second types of sensors shown in FIG. 3A and FIG. 3B combined.

FIG. 3A, FIG. 3B, and FIG. 4 illustrate a preferred method and structure for exciting and sensing acoustic vibrations in resonators 100, 600 and 800 in accordance with the embodiments of the present invention. FIG. 3A shows a first type of EMAT having a solenoid coil 302 wound around central section 101. The EMAT shown in FIG. 3A is used to excite and detect flexural modes in central section 101. Solenoid coil 302 has two ends 303 that are used to apply current and to take measurements. Resonator 100 with solenoid coil 302 in place is positioned between two permanent magnets 301 so that opposite polarity poles face the outer surface of central section 101 at 180 degree orientation from each other. In other words, a North pole of one magnet 301 faces a south pole of another magnet 301.

FIG. 3B, shows a second type of EMAT having a rectangular spiral coil 304 used to excite and detect torsional modes in central section 101. Spiral coil 304 comprises a continuous wire wound to provide radial segments 306 and axial segments 308. Two ends 307 of spiral coil 304 are used to apply excitation current and to make impedance measurements. Axial segments 308 are aligned with the pole ends of magnets 301 at positions 180 degrees apart on the circumference of central section 101. As current passes through spiral coil 304, current in each axial segment 308 on the top of the structure shown in FIG. 3B is flowing in the same direction. Likewise, current in each of the axial segments 308 at the bottom of the structure shown in FIG. 3B flows in an opposite direction from the current flow in the upper axial segments 308. Radial segments 306 are not used to excite acoustic waves and so are located as far as practical from magnets 301 to avoid excitation/detection of undesirable modes.

The preferred implementation uses just two magnets 301. More than two magnets can be used. The uniformity of forces on central section 101 may be an issue with the torsional modes, but is not an issue with the flexural modes. Hence, the use of additional magnets is contemplated as an equivalent of the preferred example illustrated and described herein.

FIG. 4 includes both types of EMAT sensors shown in FIG. 3A and FIG. 3B superimposed on a single resonator 100. As can be seen, axial segments 308 of spiral coil 304 are aligned with the pole ends of magnets 301 and are spaced from the surface of magnets 301 and central section 101. Solenoid coil 302 is positioned between spiral coil 304 and the surface of central section 101.

In the experimental structure, solenoid coil 302 had a length of 5.1 cm (measured along the axis of resonator 100). Coil 302 does not contact center section 101 but instead is maintained at a fixed close distance, for example 0.2 to 0.5 millimeter. This prevents physical damping caused by coil 302 and improves performance of the force sensor in accordance with the present invention. Magnets 301 were 5.1 cm×5.1 cm×2.5 cm permanent NdFeB magnets. Spiral coil 304 was wound flat then bent around the sample surrounding solenoid coil 302 such that the axial segments 308 pass under each magnet and a current passing through spiral coil 304 flows in opposite directions on the two opposite sides of central section 101.

Solenoid coil 302 and spiral coil 304 are each coupled to a variable frequency, continuous wave signal source (not shown) in a preferred embodiment. As current passes through each of coils 302 and 304, eddy currents are established in central section 101 creating acoustic vibrations in central section 101 by interacting with the magnetic field supplied by magnets 301. Where the frequency of electrical energy applied to solenoid coil 302 matches a resonant frequency of a flexural mode in central section 101, the electromagnetic energy coupled from coil 302 constructively reinforces the acoustic vibrations in central section 101 creating a large amplitude flexural mode resonance. Similarly, where the frequency of electrical energy applied to spiral coil 304 matches a resonant frequency of a torsional mode in central section 101, a large amplitude torsional mode resonance is excited in central section 101.

Solenoid coil 302 and spiral coil 304 can detect the resonances in a similar manner. At a vibrational resonance, the real part of the measured complex impedance of coils 302 and 304 passes through a local maxima. Desirably, a capacitor (not shown) is coupled in parallel to each of coils 302 and 304 to eliminate the imaginary portion of the complex impedance to increase the signal-to-noise ratio. Preferably, separate impedance analyzers or impedance measurement circuitry are used to simultaneously measure impedance of each of the coils 302 and 304.

Alternatively, separate coils can be used to excite and detect resonances. Such an implementation would require twice as many coils and will increase complexity and assembly cost, however, could simplify drive/detector circuitry.

Figure 5A:
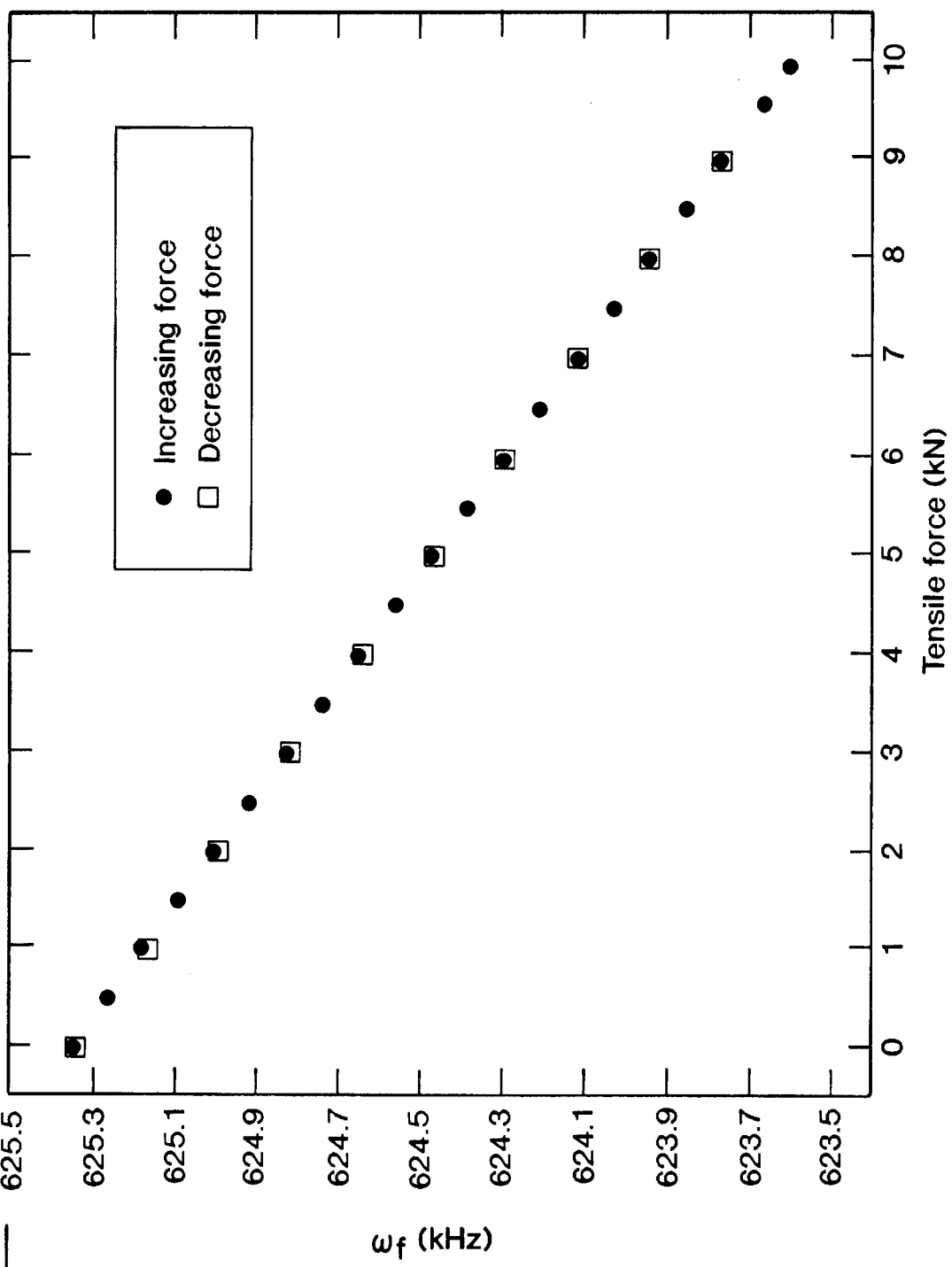
FIG. 5A is a frequency response curve for experimental studies performed in accordance with the teachings of the present invention for the flexural mode excited by the configuration shown in FIG. 3A.
Figure 5B:
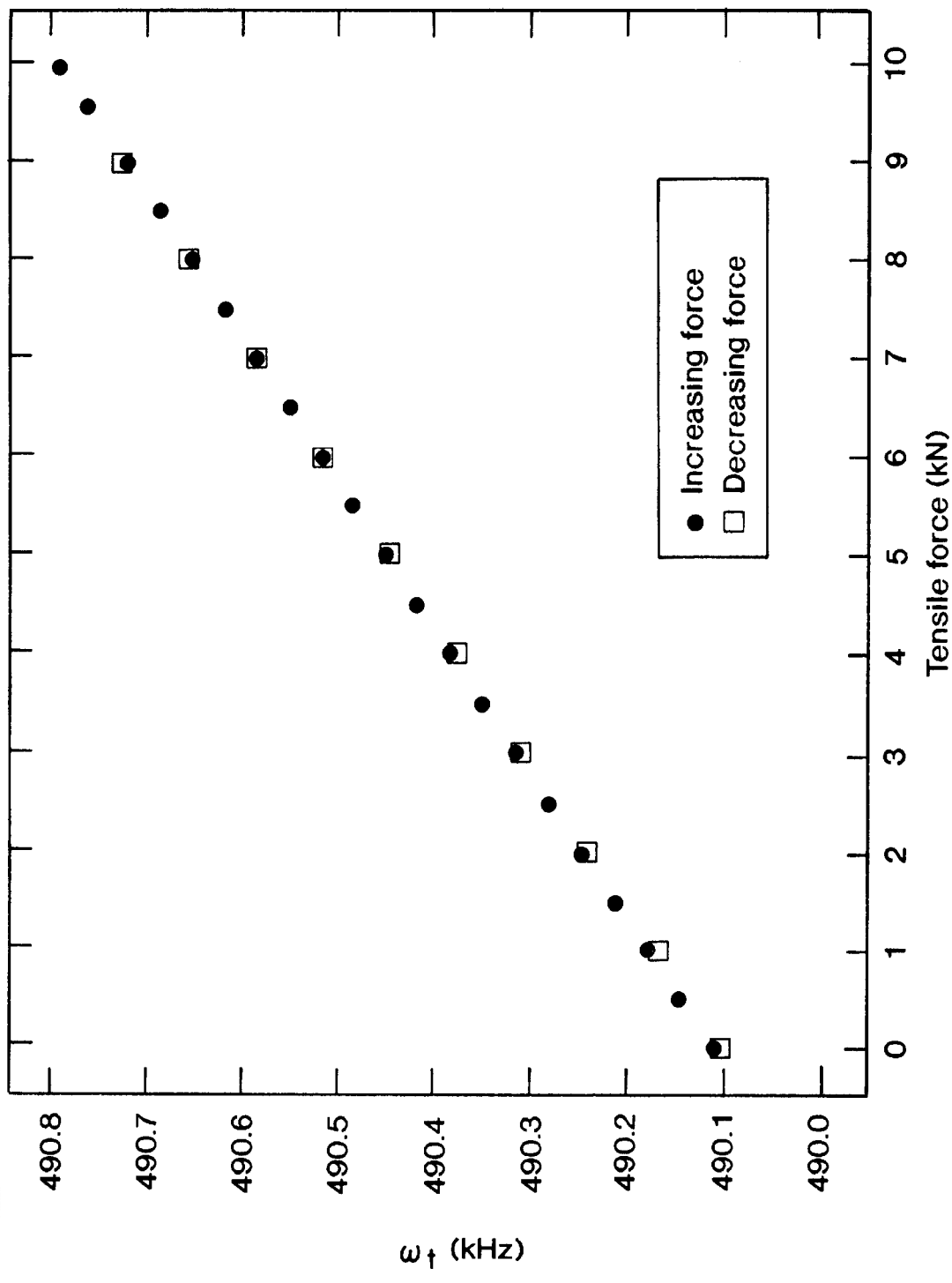
FIG. 5B is a frequency response curve for experimental studies performed in accordance with the teachings of the present invention for the torsional mode excited by the configuration shown in FIG. 3B.

FIG. 5A shows a sample output comparing resonant frequency of a flexural mode ($\omega_f/2\pi$) on the vertical axis with variation in applied tensile force on the horizontal axis. Hence, FIG. 5A illustrates results from using solenoid coil 302 shown in FIG. 3A. In FIG. 5A and FIG. 5B data points indicated by a solid circle were taken as force was increased from 0 to 10 kN while data points indicated by hollow boxes were taken while force was decreased. It can be seen from FIG. 5A that as applied force is increased $\omega_f$ decreases substantially linearly. Similarly, FIG. 5B shows a sample output comparing resonant frequency of a torsional mode ($\omega_t/2\pi$) on the vertical axis with variation of applied tensile force. As applied force is increased FIG. 5B shows that the resonant frequency of the trapped torsional mode increases substantially linearly.

While detection of resonance has been described in terms of complex impedance which may require complex impedance analyzers to detect, it should be apparent that simple electronic circuitry can be used to detect the fundamental signals in practical applications. Practical applications do not require that the change in impedance or absolute value of frequency be quantified as detection of resonance and change in resonant frequency is all that is significant. Straightforward feedback electronics and control circuitry can be used to vary the frequency of the excitation current to keep central section 101 in resonance as monitored. The change in resonant frequencies can be continuously or periodically monitored to determine stress in force sensor 100.

5. Alternative Embodiments

FIG. 6–FIG. 9 illustrate various modifications of the basic structure discussed above. Resonator 600 shown in FIG. 6 and FIG. 7 differs from resonator 100 in that the transition of interface 701 between central section 601 and distal sections 602 are gradual rather than abrupt. Experiments have shown that a gradual tapering also results in trapped resonant modes in central section 601. Other design considerations are similar to that discussed above in reference to resonator 100.

FIG. 8 and FIG. 9 shows another alternative embodiment in which resonator 800 is a hollow cylindrical tube. The relative geometries and construction of central section 801 and distal sections 802 are similar to that set out for the other embodiments. Preferably, an interior surface of resonator 800 is smooth. In other words, although there is a diameter change (either abrupt or gradual) in the outer surface of resonator 800 between central section 801 and distal sections 802, the interior diameter is constant. A step in the interior surface may also be used to provide resonant trapping, but fabrication of such a resonator is more difficult.

Wall thickness of central section 801 and distal sections 802 is selected to provide the desired response to stress. As compared to a solid cylinder, the hollow tube resonator 800 will react more (i.e., the acoustic velocity will change more) in response to force applied to mounting surfaces 803, because the cross sectional area is smaller. This feature is useful in sensing smaller forces.

An important application for the hollow tube resonator 800 is in machinery where weight is important such as aircraft. Also, drive shafts may be hollow to reduce rotational inertia. As suggested in FIG. 8, resonator 800 can be formed in a continuous pipe or tube by providing a thickened portion to the wall to form central section 801. In this manner, the present invention can be implemented with little impact on an existing machine design.

Another application for hollow tube resonator 800 is to measure the pressure of a static or moving fluid enclosed within resonator 800. The enclosed fluid may be gas or liquid. In the case of a moving fluid, resonator 800 is desirably formed as an integral part of pipeline transporting the fluid. In the case of a static fluid, one end of resonator 800 may be sealed. For example, a cap (not shown) can be screwed onto threads of one mounting surface 803 while the other mounting surface 803 is attached to a pressurized fluid reservoir (not shown).

FIG. 10 illustrates an embodiment of the present invention formed with constant diameter throughout central section 1001 and distal sections 1002. In this embodiment different material compositions are selected for central section 1001 as compared to the distal sections 1002. It is believed that by forming central section 101 with an elastic constant that differs from the elastic constant of distal sections 1002, resonant mode trapping can be further enhanced.

This embodiment of the present invention has the advantage of eliminating mode mixing caused by large diameter differences between the central section 101 and distal section 102 of the prior embodiments. It is believed that the difference in elastic constant should be about one percent or greater. Commercially available aluminum alloys are known to have elastic constants that vary over this range from one alloy to another.

Assembly and formation of a cylindrical body resonator 1000 with variable elastic constants is more complex than the other embodiments. One method of assembling resonator 1000 is to friction weld three metal cylinders of selected aluminum alloys such that the central section 1001 has a different elastic constant than distal sections 1002. Also, it is contemplated that mode trapping could be accomplished by thermally and chemically treating portions of a solid or hollow cylinder to selectively alter the elastic constant.

The advantages of the multiple elastic constant embodiment are that an abrupt, large difference in elastic constant is possible that will increase mode trapping efficiency as compared to the variable diameter embodiments. Much smaller resonant structures can be formed due to the increased efficiency. Unlike the variable diameter embodiments, a large change in elastic constant will not cause mode mixing. It is contemplated that alloys can be found and engineered that will provide more than 2% difference in elastic constants that can be joined together to form a resonator 1000 in accordance with the present invention.

Each of the embodiments shown may be modified by using different material compositions for central sections as compared to the distal sections. Using resonator 100 as an example, it is believed that by forming central section 101 with an elastic constant that differs from the elastic constant of distal sections 102, resonant mode trapping can be further enhanced. It is contemplated that an abrupt step 201 (shown in FIG. 2) or gradual step 701 shown in FIG. 7 can be used if the elastic constants differ at interfaces 201 and 701. The embodiment of the present invention shown in FIG. 10 has the advantage of reducing mode mixing generated by the abrupt or gradual radius change. However, assembly and formation of a cylindrical body resonator with variable elastic constants is difficult and may be prohibitively expensive. It is possible, though, that mode trapping could be accomplished by thermally treating portions of a solid or hollow cylinder to selectively alter the elastic constant.

6. Temperature Compensation

Figure 11:
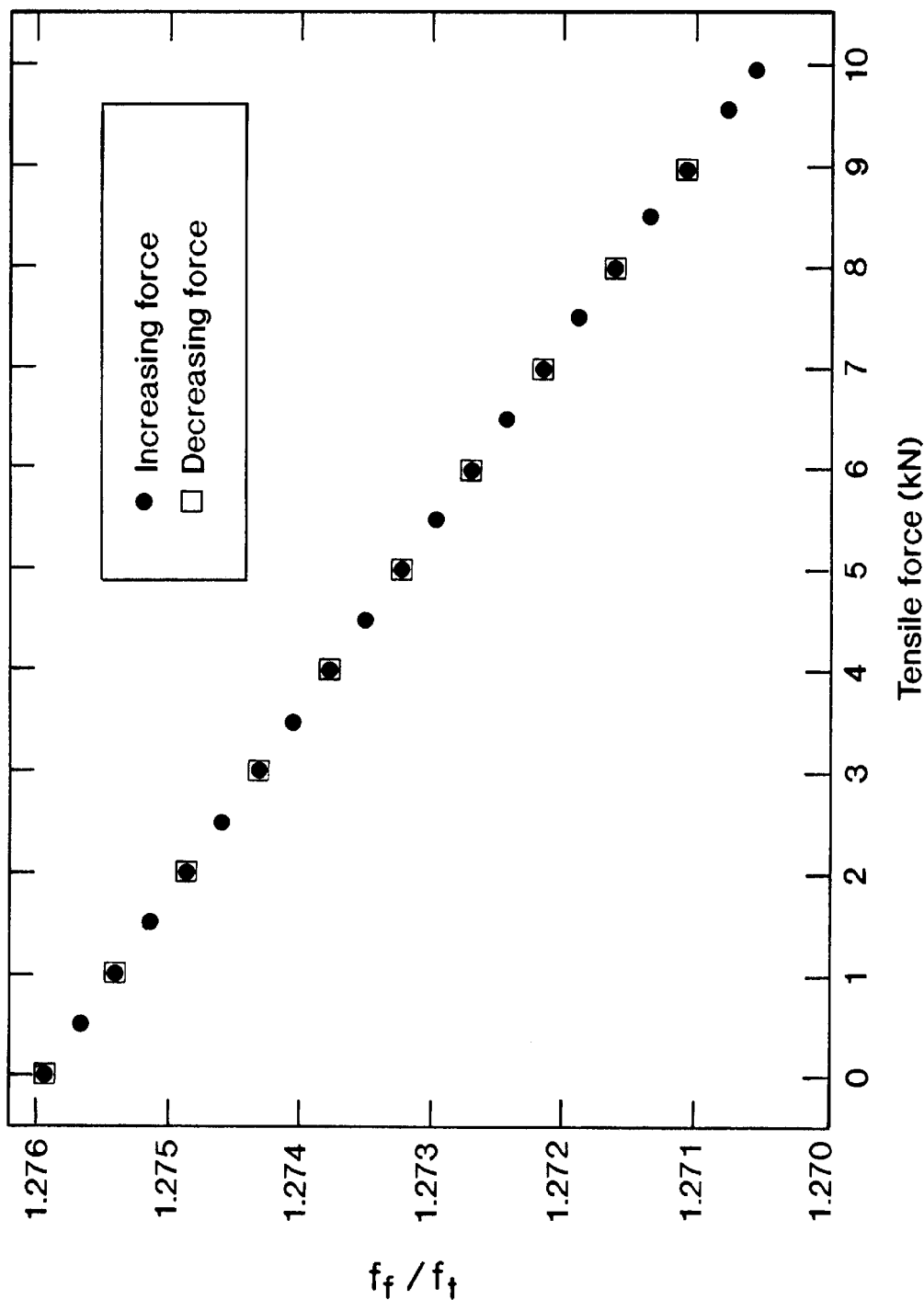
FIG. 11 is a temperature compensated response curve using the apparatus and method in accordance with the present invention.

One complication arises from the fact that resonant frequencies in cylinders are strongly dependent on temperature which varies with time unless carefully controlled. By measuring the frequencies of two modes, temperature compensation can be provided. Specifically, the ratio of flexural resonant frequency to a torsional frequency is nearly independent of temperature but changes with applied force. FIG. 11 illustrates a response curve calculated by the ratio of $\omega_f/\omega_t$. This calculated response curve exhibits substantially the same response, but has been found to be temperature compensated also.

The preferred EMAT excitation illustrated in FIG. 3A and FIG. 3B is useful in exciting and detecting both torsional and axial-sheer modes. Simple control and computational electronics are available and discussed in the references cited herein that can compute the desired temperature compensated response curve such as shown in FIG. 11.

7. Conclusion

While the present invention is described in terms of specific examples and embodiments, it is contemplated that many alternatives, modifications, and variations are possible while keeping with the essential teaching of the present invention. It is to be expressly understood that the claimed invention is not to be limited to the description of the preferred embodiments but encompasses these modifications and alterations within the scope and spirit of the inventive concept.

We claim:

1. An acoustic resonator for measuring force comprising:
a cylindrical body having:
a central section with a first radius (a) comprising a material having a plane-wave shear velocity $v_a$; and
two distal sections with a second radius (b) comprising a material having a plane-wave shear velocity $v_b$ wherein the ratio $a/v_a$ differs from the ratio $b/v_b$ by an amount selected to trap some acoustic resonant modes in the central section.

2. The acoustic resonator of claim 1 wherein $v_a < v_b$ and a=b.

3. The acoustic resonator of claim 1 wherein a resonant mode exists in the central section such that displacement amplitude of the resonant mode decays exponentially in the distal sections.

4. The acoustic resonator of claim 1 wherein the cylindrical body comprises a hollow metal tube.

5. The acoustic resonator of claim 1 wherein the central section comprises a material adapted to receive electromagnetic energy and convert the received electromagnetic energy into mechanical energy.

6. An acoustic resonator for measuring force comprising:
a cylindrical body having:
a central section with a first radius (a) comprising a material having a plane-wave shear velocity $v_a$; and
two distal sections with a second radius (b) comprising a material having a plane-wave shear velocity $v_b$, wherein the ratio $a/v_a$ differs from the ratio $b/v_b$, $v_a = v_b$ and $a > b$.

7. An acoustic resonator for measuring force comprising:
a cylindrical body having:
a central section with a first radius (a) comprising a material having a plane-wave shear velocity $v_a$;
two distal sections with a second radius (b) comprising a material having a plane-wave shear velocity $v_b$ wherein the ratio $a/v_a$ differs from the ratio $b/v_b$; and
means for applying force to the cylindrical body through at least one of the distal sections.

8. An acoustic resonator for measuring force comprising:
a cylindrical body having:
a central section with a first radius (a) comprising a material having a plane-wave shear velocity $v_a$;
two distal sections with a second radius (b) comprising a material having a plane-wave shear velocity $v_b$ wherein the ratio $a/v_a$ differs from the ratio $b/v_b$; and
transition regions between the central section and each of the two distal sections wherein the diameter of the transition regions is graduated from the first radius (a) to the second radius (b).

9. An acoustic resonator for measuring force comprising:
a cylindrical body, wherein the cylindrical body comprises a solid metal cylinder having:
a central section with a first radius (a) comprising a material having a plane-wave shear velocity $v_a$; and
two distal sections with a second radius (b) comprising a material having a plane-wave shear velocity $v_b$.

10. An acoustic resonator for measuring force comprising:
a cylindrical body having:
a central section with a first radius (a) comprising a material having a plane-wave shear velocity $v_a$;
two distal sections with a second radius (b) comprising a material having a plane-wave shear velocity $v_b$ wherein the ratio $a/v_a$ differs from the ratio $b/v_b$;
a plurality of permanent magnets surrounding the central section so that alternating North-South poles of the permanent magnets face a surface of the central section; and
an electromechanical acoustic transducer (EMAT) sensor comprising both a first coil for torsional modes and a second coil for flexural modes, the EMAT sensor being positioned around the central section between the surface of the central section and the plurality of permanent magnets.

11. A force sensor comprising:
a cylindrical body having a central section and two distal sections wherein a diameter of the central section is larger than a diameter of the distal sections;
two permanent magnets positioned about the circumference of the central section such that alternating north-south poles of the permanent magnets face the surface of the central section;
a coil positioned around the central section between the surface of the central section and the two permanent magnets, the coil having inputs for receiving a first excitation signal.

12. The force sensor of claim 11 wherein the coil is a spiral coil having sections that are substantially oriented in an axial direction with respect to the cylindrical body and aligned to the pole end of the magnets.

13. The force sensor of claim 11 wherein the coil is a solenoid coil.

14. The force sensor of claim 11 wherein the coil is a spiral coil having sections that are substantially oriented in an axial direction with respect to the cylindrical body and aligned equidistant between the pole ends of the magnets.

15. The force sensor of claim 12 further comprising:
a solenoid coil, positioned around the central section between the surface of the central section and the plurality of permanent magnets, the solenoid coil having inputs for receiving a second excitation signal.

16. The force sensor of claim 11 wherein the cylindrical body comprises metal.

17. An acoustic resonator comprising:
a cylindrical body having a central section and two distal sections; and
means for substantially trapping selected acoustic resonant modes in the central section.

18. The acoustic resonator of claim 17 wherein the means for substantially trapping comprises a gradual change in diameter of the cylindrical body at an interface between the central section and each of the two distal sections.

19. The acoustic resonator of claim 17 wherein the means for substantially trapping comprises an elastic constant change at an interface between the central section and each of the two distal sections.

20. An acoustic resonator comprising:
a cylindrical body having a central section and two distal sections;
means for substantially trapping selected acoustic resonant modes in the central section, wherein the means for substantially trapping comprises an abrupt change in diameter of the cylindrical body at an interface between the central section and each of the two distal sections.

21. An acoustic resonator comprising:
a cylindrical body having a central section and two distal sections;
means for substantially trapping selected acoustic resonant modes in the central section, wherein the means for substantially trapping comprises a thin film formed in intimate contact with an exterior surface of the central section.

22. An acoustic resonator comprising:
a cylindrical body having a central section and two distal sections;
means for substantially trapping selected acoustic resonant modes in the central section; and
mounting means for coupling a load to each of the distal portions.

23. A force sensor comprising:
a cylindrical body having a central section and two distal sections wherein selected resonant modes are substantially trapped in the central section and exponentially decay in the distal sections;
means for exciting the selected resonant modes in the central section;

means for detecting a resonant frequency of the selected resonant modes in the central section.

24. The force sensor of claim 23 wherein the central section of the cylindrical body is hollow and encloses a pressurized fluid and the measured resonant frequency changes with pressure of the enclosed fluid.

25. The force sensor of claim 23 further comprising:

means on the distal ends for applying torque to the cylindrical body whereby the measured resonant frequency changes with applied torque.

26. The force sensor of claim 23 further comprising means on the distal ends for applying axial force to the cylindrical body whereby the measured resonant frequency changes with applied axial force.

27. The force sensor of claim 23 wherein the non-contact means for exciting excites both torsional modes and flexural modes and the non-contact means for measuring measures resonant frequency of the torsional modes and flexural modes, and the force sensor further comprises:

means for mathematically combining the measured resonant frequencies of the torsional and flexural modes to provide temperature compensation.

28. The force sensor of claim 23 wherein the means for measuring comprises a direct digital measurement of resonant frequency.

* * * * *